United States Patent [19]

Sumner, Jr. et al.

[11] Patent Number: 4,804,777
[45] Date of Patent: Feb. 14, 1989

[54] PROCESS FOR THE PREPARATION OF ARYLOXYACETIC ACID

[75] Inventors: Charles E. Sumner, Jr., Kingsport; Eric J. Fugate, Jonesborough, both of Tenn.

[73] Assignee: Eastman Kodak Company, Rochester, N.Y.

[21] Appl. No.: 106,302

[22] Filed: Oct. 9, 1987

[51] Int. Cl.$^4$ .............................................. C07C 51/16
[52] U.S. Cl. ..................................... 562/421; 560/61; 560/56; 560/62; 562/471; 562/472
[58] Field of Search ......................................... 562/421

[56] References Cited

U.S. PATENT DOCUMENTS 4,238,625 12/1980 Fiege et al. ........................ 562/421

FOREIGN PATENT DOCUMENTS 2010233 1/1977 Japan .................................... 562/421

Primary Examiner—Paul J. Killos
Attorney, Agent, or Firm—Charles R. Martin; William P. Heath, Jr.

[57] ABSTRACT

Process for the preparation of an aryloxyacetic acid by oxidation of aryloxyethanol of the formula:

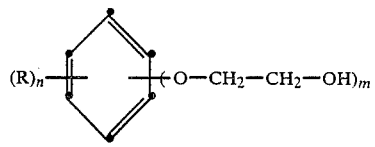

wherein
m represents 1 or 2,
n represents the numeral which results from the difference between 6 and m and R either individually or independently of one another represents hydrogen, alkyl, cycloalky, aryl, aralkyl, alkoxy, cycloalkoxy, aryloxy, halogen, alkylcarbonyl, arylcarbonyl, carboxyl or nitro, or represents a benzene ring fused to the phenyl ring, in an aqueous alkaline reaction medium at a temperature in the range of 0° C. to the boiling point of the reaction medium in the presence of a catalytic amount of a catalyst comprised of palladium, silver and optionally antimony, and carbon to form the corresponding alkali metal ester and contacting the alkali metal with a mineral acid.

12 Claims, No Drawings

PROCESS FOR THE PREPARATION OF ARYLOXYACETIC ACID

The invention relates to a process for the preparation of aryloxyacetic acids by oxidation of aryloxyethanols.

The oxidation of aryloxyethanols to corresponding acids is well known in the art. For example, U.S. Pat. No. 4,238,625 discloses such an oxidation using a catalyst comprised of palladium and other metals. Oxidation using a palladium and silver catalyst is disclosed in U.S. Pat. No. 4,247,716.

We have now discovered that yields of acid can be significantly inhanced if a combination of palladium and silver and, optionally, antimony is used instead of palladium alone or in conjunction with other metals disclosed in the prior art.

The process of our invention is composed of three steps. In the first step the aryloxyethanol is oxidized to the corresponding alkali metal aryloxyacetate using a palladium and silver and, optionally, antimony catalyst. The next step is to separate the alkali metal aryloxyacetate from the catalyst. The aryloxyacetic acid is then prepared by contacting the aryloxyacetate with a mineral acid.

The process of this invention can be illustrated by references to a preferred embodiment. In this embodiment resorcinol bis(β-hydroxyethyl)ether having the structure:

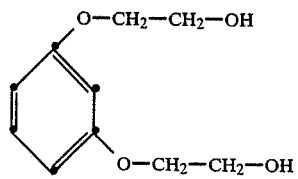

is contacted with oxygen in a sodium containing aqueous alkaline reaction medium having a pH of greater than 10 at a temperature in the range of 80° to 90° C. in the presence of 5 to 10 weight percent, based on the weight of the aryloxyethanol, of a catalyst comprised of palladium, silver and antimony on carbon wherein the mole ratio of silver to palladium to antimony is about 0.1:1:0.1. The oxidation product is the sodium ester of 1,3-phenylenedioxydiacetic acid corresponding to the structure:

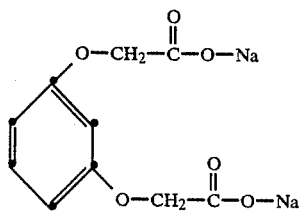

Next, the ester is separated by filtration from the catalyst. Then the ester is contacted with a mineral acid to prepare the corresponding acid corresponding to the structure:

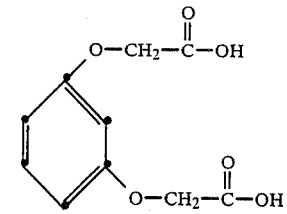

The aryloxyacetic acids prepared by the process of this invention correspond to the structure:

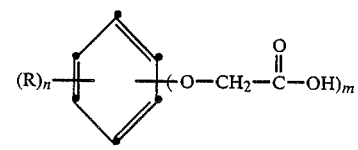

wherein
  m represents 1 or 2,
  n represents the numeral which results from the difference between 6 and m and R either individually or independently of one another represents hydrogen, alkyl, cycloalkyl, aryl, aralkyl, alkoxy, cycloalkoxy, aryloxy, halogen, alkylcarbonyl, arylcarbonyl, carboxyl or nitro, or represents a benzene ring fused to the phenyl ring.

Alkyl radicals can be straight-chain or branched hydrocarbon radicals with 1 to 12, preferably 1 to 6, carbon atoms. Preferred alkyl radicals for the process according to the invention are lower alkyl radicals. Examples of alkyl radicals which may be mentioned are methyl, ethyl, propyl, isopropyl, butyl, isobutyl, sec.-butyl, tert.-butyl, pentyl, isopentyl, tert. amyl, hexyl, isohexyl, heptyl, isoheptyl, tert.-octyl, isooctyl, nonyl, isononyl, decyl, isodecyl, undecyl, isoundecyl, dodecyl and isododecyl.

Cycloalkyl radicals can be cyclic hydrocarbon radicals with 4 to 9, preferably 5 and 6, carbon atoms. The cyclopentyl and the cyclohexyl radical may be mentioned as examples.

The phenyl and the naphthyl radical may be mentioned as preferred aryl radicals for the process according to the invention.

Aralkyl radicals can be alkyl radicals with 1 to 6 carbon atoms, preferably lower alkyl radicals, which are substituted by an aromatic hydrocarbon radical with 6 to 12 carbon atoms, preferably phenyl and naphthyl. Benzyl, a,a-dimethyl-benzyl groups may be mentioned by way of example.

Alkoxy radicals can consist of up to 12, preferably of up to 6, carbon atoms in the aliphatic part. A lower alkoxy radical is particularly preferred. The following may be mentioned as examples of alkoxy radical: methoxy, ethoxy, propoxy, isopropoxy, butoxy, isobutoxy, tert-butoxy, pentoxy, isopentoxy, hexoxy, isohexoxy and methylenedioxy.

The cyclopentoxy and the cyclohexoxy radical may be mentioned as preferred cycloalkoxy radicals.

The phenoxy and the naphthoxy radical may be mentioned as preferred aryloxy radicals.

Halogens can be fluorine, chlorine, bromine and iodine, preferably chlorine and bromine.

Lower alkylcarbonyl radicals ($C_1$ to $C_6$), such as the acetyl radical, may be mentioned as preferred alkylcarbonyl radicals.

The benzoyl radical may be mentioned as a preferred arylcarbonyl radical.

Fusion of a benzene ring to the phenyl ring can, for example, produce the naphthalene ring system.

Fusion of a cycloalkane ring to the phenyl ring can, for example, produce the tetralin ring system.

It is of course possible for the abovementioned substituents to be substituted by usual radicals which are inert under the reaction conditions. Fluorine, chlorine, methyl and methoxy may be mentioned as examples.

One preferred embodiment is where n is 4, R is hydrogen and m is 2. A particular preferred embodiment is the meta and para isomer, with the meta being most preferred. Another preferred embodiment is where R represents a benzene ring fused to the phenyl ring to the naphthalene structure and m is 2. A particularly preferred embodiment is the 2,6-isomer.

The aryloxyethanols which are used to prepare the aryloxyacetic acids are prepared by methods well known in the art. For example, the aryloxyethanols can be prepared by addition reaction of ethylene oxide with the hydroxyl group or groups of an appropriately substituted phenol or naphthol (Monatshefte Chemie 77, (1947) 80 to 85).

Representative examples of aryloxyethanols are phenoxyethanol, 2-methyl-phenoxyethanol, 3-methyl-phenoxyethanol, 4-methyl-phenoxyethanol, 2,3-dimethyl-phenoxyethanol, 2,4-dimethyl-phenoxyethanol, 2,5-dimethyl-phenoxyethanol, 2,6-dimethyl-phenoxyethanol, 3,4-dimethyl-phenoxyethanol, 3,5-dimethyl-phenoxyethanol, 2-chloro-phenoxyethanol, 3-chloro-phenoxyethanol, 4-chloro-phenoxyethanol, 2-chloro-4-methyl-phenoxyethanol, 2-chloro-5-methyl-phenoxyethanol, 2-chloro-6-methyl-phenoxyethanol, 4-chloro-2-methyl-phenoxyethanol, 4-chloro-3-methyl-phenoxyethanol, 2-chloro-4-fluoro-phenoxyethanol, 2,3-dichloro-phenoxyethanol, 2,4-dichloro-phenoxyethanol, 2,5-dichloro-phenoxyethanol, 2,6-dichloro-phenoxyethanol, 3,4-dichloro-phenoxyethanol, 3,5-dichloro-phenoxyethanol, 4,6-dichloro-2-methyl-phenoxyethanol, 2,6-dichloro-4-methyl-phenoxyethanol, 2,6-dichloro-3-methyl-phenoxyethanol, 2,4-dimethyl-6-chloro-phenoxyethanol, 2,6-dimethyl-4-chloro-phenoxyethanol, 2,4,5-trichloro-phenoxyethanol, 2,4,6-trichloro-phenoxyethanol, 2,4,6-trichlorophenoxyethanol, 3,4,5-trichloro-phenoxyethanol, 2,3,4-trichloro-phenoxyethanol, 4-nonylphenoxyethanol, α-naphthoxyethanol and β-naphthoxyethanol. Preferred aryloxyethanols for the process according to the invention are phenoxyethanol, 4-chloro-2-methyl-phenoxyethanol, 2,4-dichloro-phenoxyethanol and 2,4,5-trichloro-phenoxyethanol.

The first step of the process of this invention is conducted by bringing oxygen or a oxygen-containing gas, such as air, into good contact with the aryloxyethanol in an aqueous medium, which also contains the source of the alkali metal cation and the catalyst. The reaction medium can be a solution or a suspension; however, a solution is preferred.

In general, the reaction is carried out at atmospheric pressure, but oxidation can also be carried out at higher or lower pressures. In general, the process according to the invention is carried out in the pressure range of 0.5–10 bar.

The aryloxyacetate compound which results from the first step of the invention corresponds to the structure:

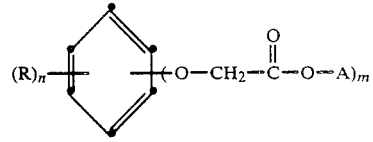

wherein n, m and R are as described above and A is an alkali metal cation.

It is important that the catalyst be separated from the aryloxyacetate. This can be accomplished by method well known in the art, such as centrifugation or filtration. Due to cost, filtration is perferred.

The aryloxyacetate which is separated from the catalyst is then converted into the corresponding aryloxyacetic acid by contact with a mineral acid according to techniques well known in the art, such as disclosed in U.S. Pat. No. 4,238,625.

The palladium useful in the catalyst of this invention can be in a variety of forms. Elemental palladium metal can be used. Other palladium compounds, such as the oxides can be used.

The silver can be used in the form of the nitrate, oxide, acetate, trifluoro acetate, tosylate, triflate, tungstate, sulfate, or tetrafluoro borate.

The antimony can be used as the acetate, oxide, or penta chloride (or any soluble form).

The carbon useful for the catalyst support is a low sulfur, pophilic, pulverulent type, which is high in silicon and has an ordered structure. Materials of this nature are well known in the art.

The relative amounts of metals in the catalyst can vary widely. Broadly, the mole ratio of silver to palladium can be 0.05 to 0.5 moles of silver per mole of palladium. Preferably the ratio is 0.05 to 0.3 with 0.1 mole most preferred. The ratio of silver to palladium is the same regardless whether antimony is used. If antimony is used, the ratio of silver to palladium to antimony is 0.05 to 0.5, preferably 0.05 to 0.3, moles of silver and 0.05 to 0.5, preferably 0.05 to 0.3, moles of antimony for each mole of palladium. The use of 0.1 mole antimony per mole of palladium is most preferred.

The catalyst useful in this invention is prepared by applying the metals to a carbon support according to methods well known in the art. According to one method, a 5-weight percent palladium on carbon catalyst is reduced and with $H_2$ an alcohol or hydrazine in an aqueous slurry followed by contacting the aqueous slurry with a solution of $AgNO_3$ in the absence of air. Optionally, this material can be contacted with $Sb_2O_3$ in water at 85° C. for 1 hour. According to another method, a catalyst was prepared by reducing palladium on carbon by heating it in water at 100° C. in the presence of resorcinol bis(2-hydroxyethyl)ether followed by the addition of antimony acetate. The resulting mixture was heated for 30 minutes and silver nitrate was added. Still another method is to impregnate a carbon support with silver nitrate and reduce the silver to silver metal. This material can be sequentially treated with $SbCl_3$ and $PdCl_2$, followed by reduction.

The amount of catalyst can vary within wide limits depending on the desired rate of oxidation. In general, the amount of catalyst is 5 to 20 weight percent, preferably 5 to 10 weight percent, based on the weight of aryloxyethanol.

Preferably the steps of the process are performed in the sequence described; however, the sequence of the steps can be modified if desired. For example, the catalyst can be added to the mixture or solution containing aqueous alkali metal and aryloxyethanol. One can also add the mixture of aqueous alkali and aryloxyethanol to the catalyst. Finally, one can also first take the catalyst, a part of the aqueous alkali metal solution and then add the aryloxyethanol together with the remaining alkali metal solution.

The oxidation step of the process of the invention is carried out in an aqueous alkalin reaction medium. Sodium hydroxide or potassium hydroxide are preferred compounds to prepare the alkali reaction medium. The amount of alkali metal cation is chosen so as to provide 1 to 6 mols of alkali metal cation per mol of carboxyl group formed.

The concentration of the aryloxyethanol in the aqueous alkaline reaction mixture is in general selected so that the resulting aryloxyacetic acid is present in solution during the reaction. Concentrations of 2% to 25% by weight are advantages. If desired, the solubility can be improved by the addition of inert solvents or solubilizing agents.

The temperature for the oxidation step can lie between 0° C. and the boiling point of the reaction mixture. The reaction temperature to be used in each individual case depends on the catalyst system, the alkali concentration, the material properties of the educts and of the products, and other factors. The temperature range of about 70° C. to about 100° C. is preferred and the range of 80° C. to 90° C. is particularly preferred.

The aryloxyacetic acids prepared by this invention are useful for the preparation of polyesters according to techniques well known in the art.

EXAMPLE 1

Resorcinol bis($\beta$-hydroxyethyl)ether (100 g; 0.51 mol) was dissolved in 1 liter of water containing NaOH (44 g; 1.1 mol). The solution was warmed to 60° and a catalyst composed of 5% Pd, 0.5% Ag on carbon (10 g) was added. The resulting slurry was transferred to a 2-liter stirred autoclave which can be operated at pressures from 25 to 350 psig and temperatures from 50° to 200° C. and is agitated by a magnetic stirrer equipped with a Rushton turbine. The autoclave was equipped with a dip tube which allowed the reaction mixture to be sampled periodically while the reaction was taking place. The mixture was stirred at 960 rpms while air was passed through the mixture at a rate of 4 scfh with a head pressure of 50 psig. The autoclave was slowly heated to 80° C. at which point an exotherm occurred, and the autoclave was cooled at such a rate to maintain the temperature of the reaction mixture at 80° to 82° C. After two hours, the temperature of the mixture dropped and the consumption of oxygen ceased. The mixture was removed from the autoclave, the catalyst was filtered off, and the filtrate was acidified with 150 mL of 20% sulfuric acid. After cooling to room temperature (about two hours), the resulting 1,3-phenylenedioxydiacetic acid was collected by filtration, washed with cold water (200 mL), dried in a vacuum oven at 80°. The yield was 104 g (91%) and the purity was >99%. The result of this and the following examples are shown in the table.

EXAMPLES 2 THROUGH 10

The procedure given in Example 1 was followed except for the amounts of silver and palladium used and the temperatures. The results are shown in the table below.

TABLE 1

| No. | % Ag | % Pd | Temp. | Time (Min) | NaOH Conc. (M) | % Yield |
|---|---|---|---|---|---|---|
| 1 | 0.5 | 5.0 | 80 | 120 | 1.10 | 91 |
| 2 | 2.5 | 5.0 | 80 | 120 | 1.10 | 81 |
| 3 | 2.5 | 5.0 | 100 | 120 | 1.10 | 96 |
| 4 | 2.5 | 5.0 | 80 | 120 | 1.10 | 91 |
| 5 | 5.0 | 5.0 | 100 | 120 | 1.10 | 94 |
| 6 | 4.0 | 5.0 | 80 | 120 | 1.10 | 75 |
| 7 | 0.5 | 5.0 | 100 | 120 | 1.10 | 91 |
| 8 | 1.0 | 10.0 | 100 | 120 | 1.10 | 89 |
| 9 | 4.0 | 5.0 | 80 | 120 | 1.10 | 65 |
| 10 | 4.0 | 5.0 | 80 | 120 | 1.65 | 91 |

EXAMPLE 11

A 0.5 L benchtop oxidation apparatus was charged with 25 g of resorcinol bis($\beta$-hydroxyethyl)ether, 11.5 g of sodium hydroxide, 2.5 g of 2.5% Ag/5% Pd on carbon catalyst, and 250 mL of water. The resulting mixture was heated to 85° C. and oxygen was introduced into the mixture while it was vigorously stirred. Over a period of 45 minutes, the reaction mixture exothermed and oxygen was consumed. The mixture was filtered while hot to remove the catalyst, and the filtrate was acidified with 8 mL of conc. sulfuric acid. (The mixture was about 50° C. when acidified.) The resulting mixture was allowed to cool to room temperature, and the product was collected by filtration and air dried. The yield of 1,3-phenylenedioxydiacetic acid was 25.8 g (90%). The product contained less than 1% of the partially oxidized product, (3-hydroxyethoxy)phenoxyacetic acid.

EXAMPLE 12

The procedure given in Example 11 was followed except the silver promoter was added to the reaction mixture by the following procedure. Resorcinol bis($\beta$-hydroxyethyl)ether (25 g) and 5% Pd on carbon support (2.5 g) were heated in 250 mL of water to 70° C. A solution of 0.040 g of silver nitrate dissolved in 5 mL of water was added while the mixture was stirred. The resulting mixture was stirred at this temperature for 10 minutes and sodium hydroxide was added. The resulting mixture was charged to the benchtop oxidizer and the procedure given in Example 11 was followed. The yield of 1,3-phenylenedioxydiacetic acid was 26.1 g (91%). The yield of (3-hydroxyethoxy)-phenoxyacetic acid was less than 1%.

EXAMPLE 13 (FOR COMPARISON)

2.5 g of 5% Pd on carbon support was reduced by refluxing in 100 mL of water under a hydrogen atmosphere for 45 minutes. The resulting catalyst was used in a procedure as described in Example 11. No silver promoter was used. The reaction stopped consuming oxygen after 24 minutes. Work-up of the reaction mixture produced 21.4 g (80%) of (3-hydroxyethoxy)-phenoxyacetic acid. Only 1.4 g of the desired product, 1,3-phenylenedioxydiacetic acid, was produced, along with 1.2 g of (3-hydroxy)phenoxyacetic acid.

EXAMPLE 14

A 0.5 L benchtop oxidation apparatus was charged with 25 g of resorcinol bis(beta-hydroxyethyl)ether, 250 mL of water, 2.5 g of 5% Pd on carbon, and 0.05 g of antimony triacetate. The resulting mixture was stirred at 95° C. for 30 minutes and cooled to 85° C. A solution of 0.02 g of silver nitrate in 3 mL of water was added and the resulting mixture was stirred for 25 minutes while the mixture was let cool to 56° C. Sodium hydroxide (11.5 g) was added, and the mixture was warmed to 82° C. and oxygen was introduced into the mixture while it was vigorously stirred. The reaction mixture exothermed to 95° while oxygen was consumed. This temperature was maintained until the consumption of oxygen ceased (33 minutes). The catalyst was filtered from the hot mixture and the resulting filtrate was acidified with 7.5 mL of conc. $H_2SO_4$. The initial filtrate was clear and colorless. The product separated from the acidified filtrate as colorless crystals. The yield was 25.9 g (91%) of 1,3-phenylenedioxydiacetic acid which was of greater than 99% purity.

We claim:

1. A process for preparation of an aryloxyacetic acid corresponding to the structure:

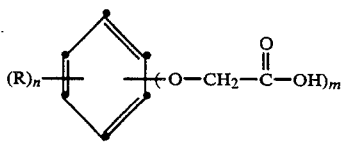

wherein m represents 1 or 2, n represents the numeral which results from the difference between 6 and m and R either individually or independently of one another represents hydrogen, alkyl, cycloalkyl, aryl, aralkyl, alkoxy, cycloalkoxy, aryloxy, halogen, alkylcarbonyl, arylcarbonyl, carboxyl or nitro, or represents a benzene ring fused to the phenyl ring, comprising
   (a) preparing an aryloxyacetate corresponding to the structure:

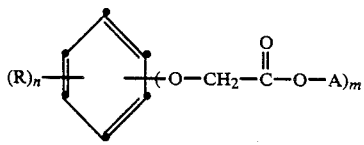

wherein n, m and R are as described above and A is an alkali metal cation by contacting an aryloxyethanol corresponding to the structure:

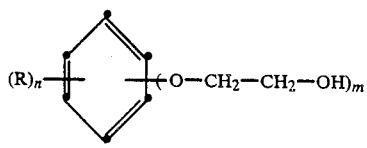

wherein m, n and R are as described above, with oxygen in an aqueous alkaline reaction medium at a temperature in the range of 0° C. to the boiling point of the reaction medium in the presence of a catalytic amount of a catalyst comprised of palladium, silver and carbon, (b) separating the aryloxyacetate from the catalyst, and
   (c) preparing the aryloxyacetic acid by contacting the separated aryloxyacetate with a mineral acid.

2. The process of claim 1 wherein R is hydrogen or a benzene ring fused to the phenyl ring.

3. The process of claim 1 wherein the pH is greater than 10.

4. The process of claim 1 wherein the temperature range is from about 70° to about 100° C.

5. The process of claim 1 wherein the amount of catalyst is 5 to 20 weight percent, based on the weight of the aryloxyethanol.

6. The process of claim 5 wherein the amount of catalyst is 5 to 10 weight percent, based on the weight of the aryloxyethanol.

7. The process of claim 1 wherein the mole ratio of silver to palladium is 0.05 to 0.5:1.

8. The process of claim 7 wherein the mole ratio of silver to palladium is 0.05 to 0.3:1.

9. The process of claim 1 wherein the catalyst additionally comprises antimony.

10. The process of claim 9 wherein the mole ratio of silver to palladium to antimony is 0.05 to 0.5:1:0.05 to 0.5.

11. The process of claim 10 wherein the mole ratio of silver to palladium to antimony is 0.05 to 0.3:1:0.05 to 0.3.

12. A process for preparation of an aryloxyacetic acid corresponding to the structure:

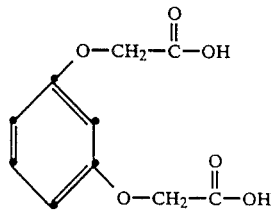

comprising
   (a) preparing an aryloxyacetate corresponding to the structure:

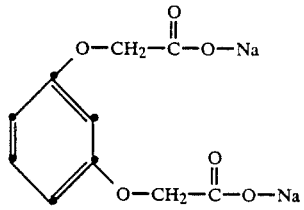

by contacting an aryloxyethanol corresponding to the structure:

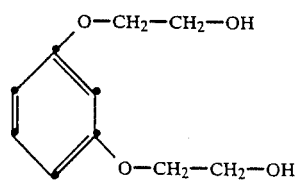

with oxygen in an aqueous alkaline reaction medium having a pH of greater than 10 at a temperature in the range of 80° to 90° C. in the presence of 5 to 10 weight percent, based on the weight of the aryloxyethanol, of a catalyst comprised of palladium, silver, antimony, and carbon wherein the mole ratio of silver to palladium to antimony is about 0.1:1:0.1, (b) separating by filtration the aryloxyacetate from the catalyst, and
(c) preparing the aryloxyacetic acid by contacting the separated aryloxyacetate with a mineral acid.

* * * * *